(12) United States Patent
Moll et al.

(10) Patent No.: US 7,354,443 B2
(45) Date of Patent: Apr. 8, 2008

(54) SURGICAL SUTURING MACHINE

(75) Inventors: Philipp Moll, Aachen (DE); Kurt Klundt, Hirschhorn (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 651 days.

(21) Appl. No.: 10/250,756

(22) PCT Filed: Mar. 25, 2002

(86) PCT No.: PCT/EP02/03242

§ 371 (c)(1),
(2), (4) Date: Jul. 2, 2003

(87) PCT Pub. No.: WO02/076304

PCT Pub. Date: Oct. 3, 2002

(65) Prior Publication Data
US 2004/0092963 A1    May 13, 2004

(30) Foreign Application Priority Data
Mar. 26, 2001    (DE)    ................................ 101 16 171

(51) Int. Cl.
*A61B 17/04* (2006.01)
(52) U.S. Cl. .................................... 606/144
(58) Field of Classification Search ................ 606/139, 606/144–150, 222–228; 112/162, 168, 169, 112/177, 187, 286
See application file for complete search history.

(56) References Cited

U.S. PATENT DOCUMENTS

| | | | | |
|---|---|---|---|---|
| 1,197,305 A | * | 9/1916 | Plumley | ...................... 112/162 |
| 2,033,693 A | * | 3/1936 | Duke | .......................... 112/162 |
| 2,580,964 A | | 1/1952 | Skaller | |
| 4,123,982 A | * | 11/1978 | Bess et al. | .................... 112/169 |
| 4,580,514 A | * | 4/1986 | Hanyu et al. | ................ 112/162 |
| 4,747,358 A | | 5/1988 | Moll et al. | |
| 4,841,888 A | | 6/1989 | Mills et al. | |
| 5,496,334 A | | 3/1996 | Klundt et al. | |
| 5,964,170 A | * | 10/1999 | Gries | .......................... 112/291 |

FOREIGN PATENT DOCUMENTS

| | | |
|---|---|---|
| DE | 43 10 555 C1 | 12/1993 |
| DE | 10116171 A1 * | 10/2002 |

\* cited by examiner

*Primary Examiner*—Todd E. Manahan
*Assistant Examiner*—Melanie Tyson
(74) *Attorney, Agent, or Firm*—McGlew and Tuttle P.C.

(57) ABSTRACT

An endoscopic suturing machine is provided with a housing, with a housing upper part (2, 4) for accommodating drives (20, 50, 60 and 80) for the stitch-forming tools (11, 12), with a housing shaft (3) adjoining same for accommodating a device for transmitting the movements generated by the drives (20, 50, 60 and 80) to the stitch-forming tools (11, 12). The forming tools include at least a needle (11) and a shuttle (12), which cooperates with the needle. The shuttle or looper can be moved after grasping the thread loop along a multidimensional path of movement from its position which is located under the material being sewn and grasps the thread loop into a position which is located above the material being sewn and in which the thread triangle formed by the thread loop led onto the upper side of the material being sewn surrounds the projection of the path of the needle (FIG. 5).

16 Claims, 8 Drawing Sheets

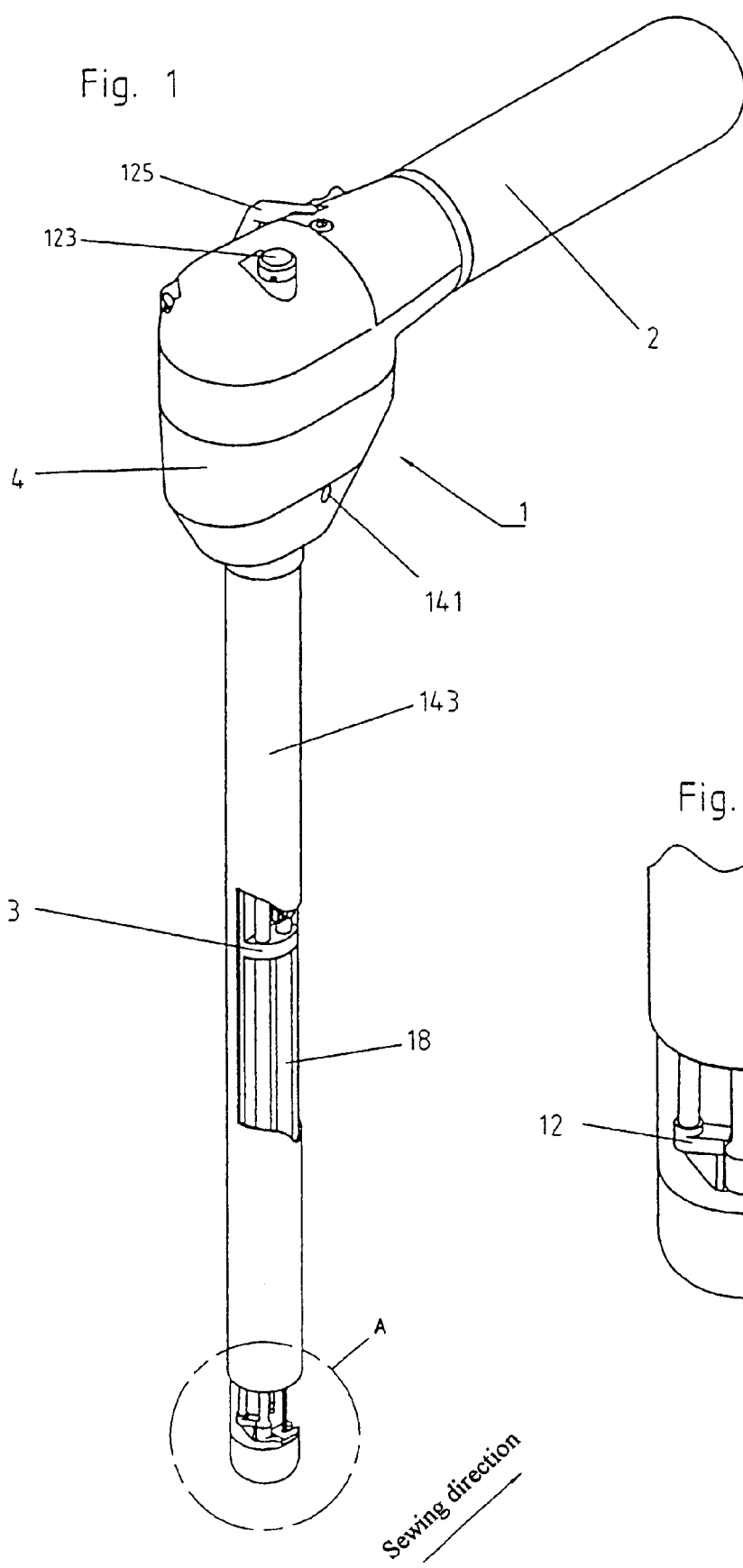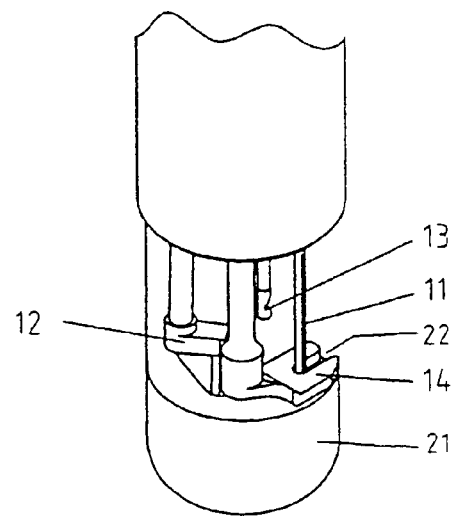

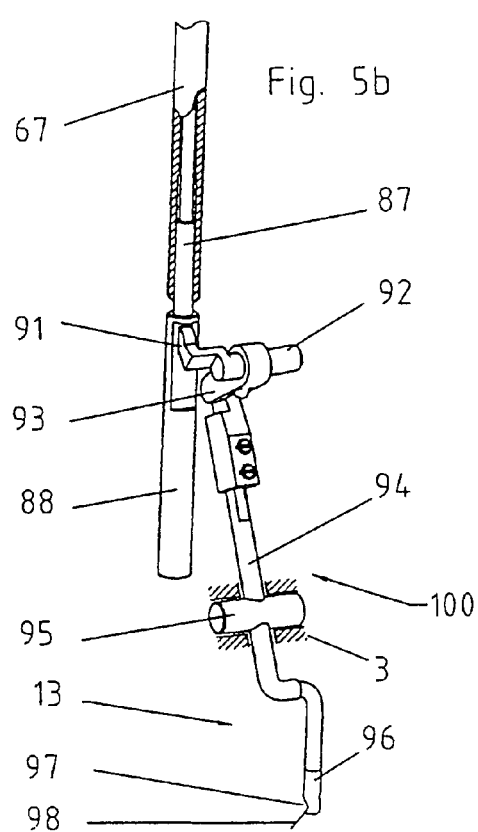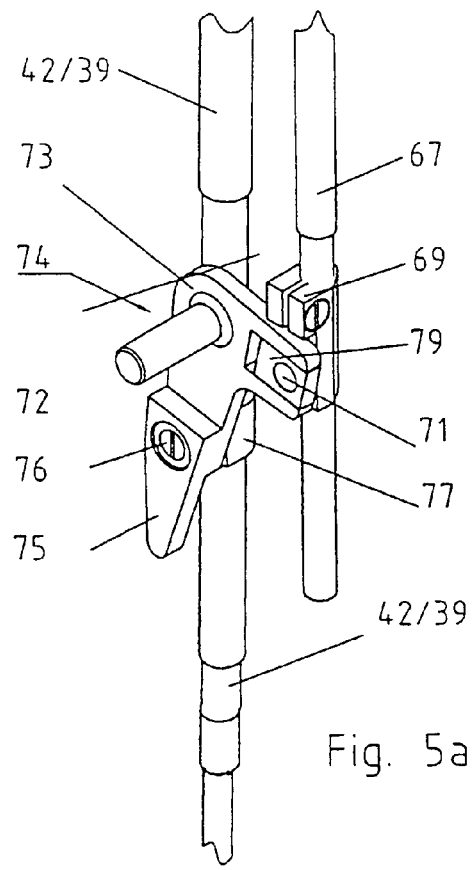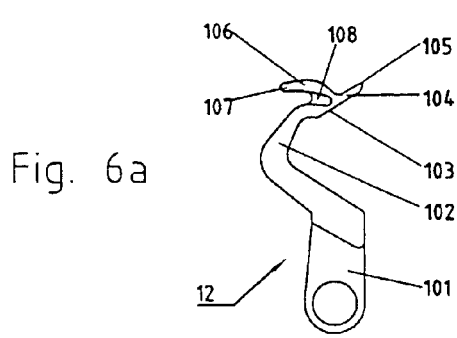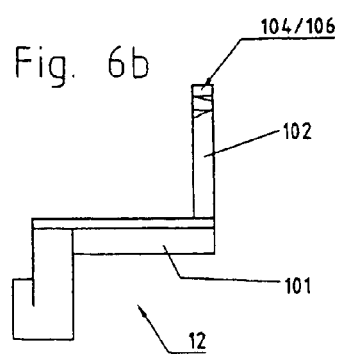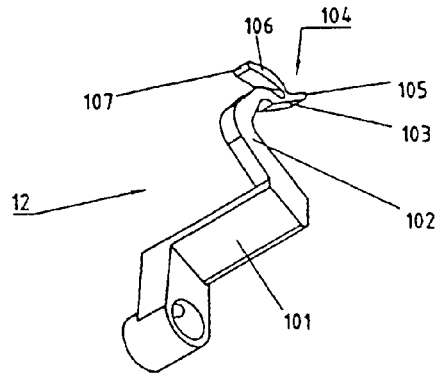

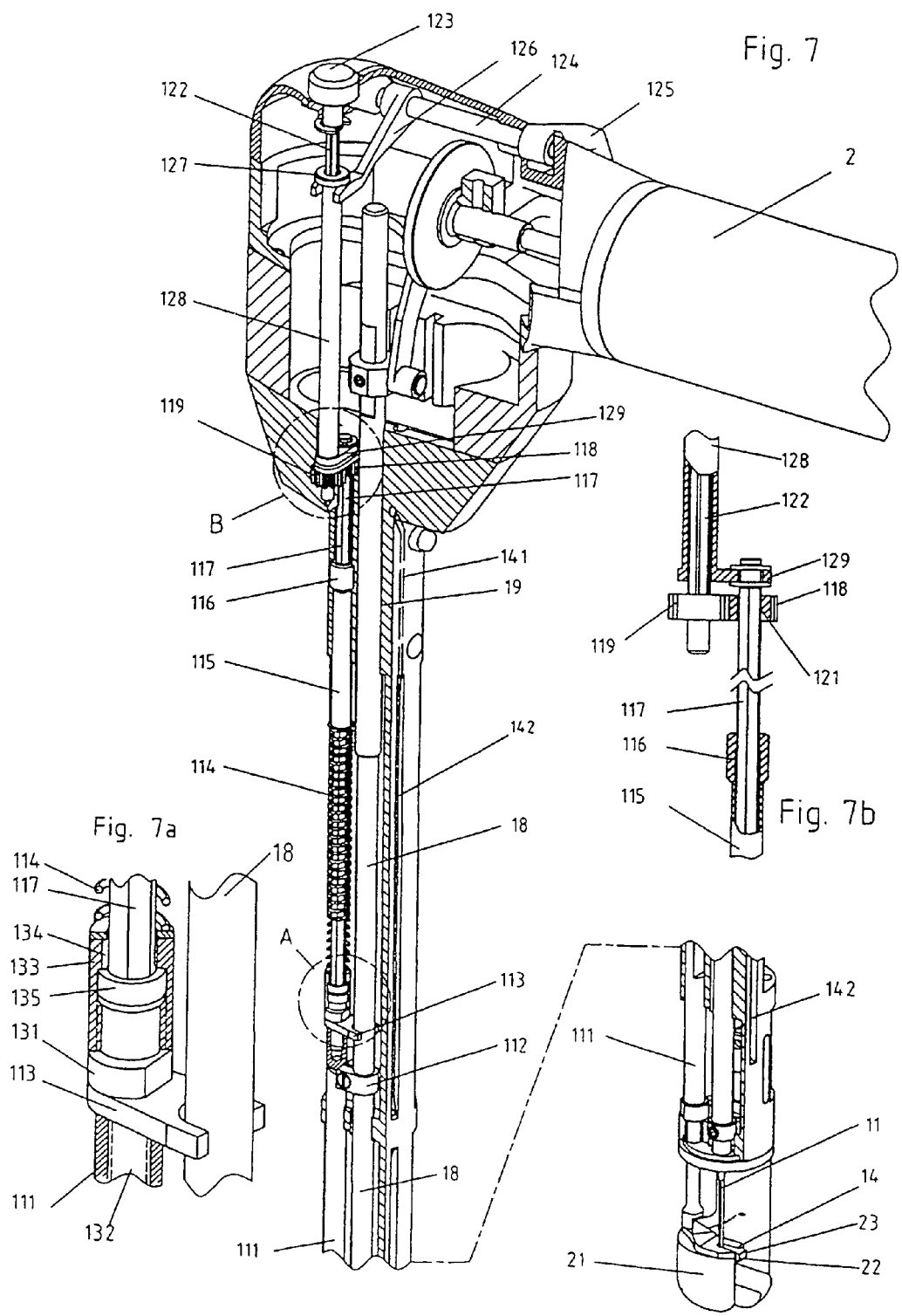

SURGICAL SUTURING MACHINE

FIELD OF THE INVENTION

The present invention pertains to a surgical suturing machine, especially a suturing machine for preparing sutures within the human or animal body.

BACKGROUND OF THE INVENTION

Suturing machines of this type shall have the smallest possible overall volume because they must be introduced into the human or animal body, and not only the operational controls proper, but possibly also the drives for the stitch-forming tools are therefore arranged in a housing which remains outside the body and they are connected to the operational controls by means of transmission means.

U.S. Pat. No. 4,841,888 shows a suturing machine called an "endoscopic suturing machine" with a tubular housing, with the stitch-forming tools arranged at the end of the housing that is to be introduced into the body, and the free other end of the housing carries the operational controls, which are connected to the stitch-forming tools via transmission means arranged inside the tubular housing.

Since only single-thread chain stitch of the stitch type 101 (DIN 5300 Part 1) is to be prepared with this suturing machine, the stitch-forming tools as well as their movements are relatively simple and are formed by a needle, which is arranged longitudinally displaceably in the tubular housing and carries a thread and by a shuttle cooperating with the needle. The shuttle is formed here by an essentially V-shaped lever, which is provided as the beak of the shuttle at the end of one leg. The end of the other leg is mounted pivotably at an elastic projection of the housing, which also acts as the support surface for the beak of the shuttle at the same time. As soon as the needle has performed a loop lifting movement initiated by an actuating element of a wire-shaped design, the shuttle is pivoted into the thread loop formed by a second actuating element, which has likewise a wire-shaped design and acts on the tip of the "V." At the end of this pivoting movement, the beak of the shuttle lies on the projection, so that the thread loop grasped by the shuttle is held by the shuttle until the needle is inserted the next time, and the needle can be pushed into the thread triangle formed by the thread loop to cut off the thread loop.

Since an actuating element of a wire-shaped design each is fully sufficient both for generating the longitudinal movements of the needle and for generating the pivoting movements of the shuttle, the design effort needed for this is relatively low.

However, it is disadvantageous that only a simple chain stitch of stitch type 101 can be prepared hereby and only a simple straight suture can be prepared as a result, which is disadvantageous compared with a so-called cover-stitch suture, especially in the area of medicine.

SUMMARY OF THE INVENTION

The basic object of the present invention is therefore to provide a suturing machine which is suitable for use as an endoscopic suturing machine and which makes it possible to prepare a cover-stitch suture using a stitch type corresponding to the stitch type 501.

This object is accomplished with a suturing machine that has a housing comprising a housing upper part for receiving drives for the stitch-forming tools, a housing shaft adjoining the housing upper part for receiving transmission means for transmitting the movements generated by the drives to the stitch-forming tools, which have at least one thread-carrying needle and a shuttle, which cooperates with the needle and which can be brought, after grasping the thread loop formed by the needle, into a position that is located above the material being sewn and in which the thread triangle formed by the loop being guided on the top side of the material being sewn surrounds the projection of the path of the needle, from its position located under the material being sewn, which position grasps the thread loop, along a multidimensional path of movement.

Since the shuttle in the solution according to the present invention takes up the thread loop formed by the needle and also brings this from the grasping position located under the material being sewn first into an intermediate position located to the side of the material being sewn and from there into a position located above the plane of the material being sewn in order to subsequently position it in a position in which the path of movement of the needle extends through the thread triangle formed by the thread loop for cutting off by the needle, it is possible to use a single shuttle instead of the two-shuttle system, so that not only the second shuttle, but also the corresponding drive means for that shuttle are eliminated, and the space required for the drive of the shuttle can also be additionally reduced substantially, and the shuttle can be driven by a single drive means, namely, by the single shuttle shaft.

The path of movement of the shuttle, which is necessary for this, can be embodied in terms of design in a relatively simple manner if it is composed of a first pivoting movement taking place under the material being sewn, and a lifting movement taking place subsequently, and a second pivoting movement.

An especially compact arrangement is obtained if the shuttle shaft carrying the shuttle is arranged longitudinally displaceably and rotatably in the housing and a pivoting drive and a lifting drive are associated with it, whose drive means (cam plates) are arranged on one and the same shaft, which is aligned in parallel to the shuttle shaft.

It is advantageous in this connection for the driven part (carrier 44) of the lifting drive to be connected rigidly to the shuttle shaft in the axial direction and for the shuttle shaft to be freely rotatable in the driven part (carrier 44), on the one hand, and, on the other hand, for the driven part (bush 59) of the pivoting drive (60) to be connected to the shuttle shaft in such a way that it rotates therewith in unison, and for the shuttle shaft to be longitudinally displaceable in the axial direction in the driven part (bush 59).

To achieve the above-mentioned dual function of the shuttle, it is necessary for the lateral distance between the main blade grasping the thread loop and the needle to be substantially shorter during the grasping of the thread loop than the corresponding lateral distance from the needle during the positioning of the grasped thread loop above the material being sewn for the insertion of the needle into the thread triangle formed by the thread loop. This means that—in the direction of view from the edge of the material being sewn toward the needle—the main blade of the shuttle must be located by a certain amount behind the path of movement of the needle, because insertion of the needle into the thread triangle is guaranteed only if the needle is moving along a path that has a certain distance from the short side of the triangle formed by the thread loop.

This different position of the main blade in its respective end position can be achieved by the first pivoting movement of the shuttle, which movement is used to grasp the thread loop, taking place around an axis whose distance from the needle is greater than the distance between the needle and the axis around which the second pivoting movement used to position the thread loop on the material being sewn takes place.

This can be embodied in terms of design in a simple and compact manner by the shuttle shaft being formed by an upper part and a lower part and by the two being connected to each other by means of a hinge part such that the lower part is movable in the horizontal direction in relation to the upper part.

The pivoting movement necessary for grasping the thread loop can now take place with the lower part of the shuttle shaft pivoted out in one direction, while the pivoting movement necessary for positioning the thread loop above the material being sewn can take place with the lower part of the shuttle shaft pivoted out in the other direction, i.e., when the lower part of the shuttle shaft has moved by a certain amount toward the needle in the horizontal direction extending in parallel to the edge of the material being sewn.

To achieve the relative movement between the upper part and the lower part, which is necessary for the different deflections of the lower part of the shuttle shaft, it is useful to provide a horizontal drive, which brings about a lifting movement of a push rod, which is derived from a cam plate and can be transmitted as a horizontal movement to the lower part via a drive connection.

A generally compact arrangement is obtained if the cam plate for the horizontal drive is arranged on a shaft that is directed in parallel to the shaft accommodating the cam plates of the pivoting drive and the lifting drive, and an additional cam plate, which is used to drive a thread deflector, is arranged above the cam plates for the pivoting drive and the lifting drive.

An especially compact arrangement is obtained if the cam plate for the deflector drive actuates a rod which is arranged within the push rod in a longitudinally displaceable manner, and its end projecting from the push rod imparts a movement formed from a vertical movement component and a horizontal movement component to the thread deflector via a drive connection. Due to the coaxial arrangement of the push rod for the horizontal drive for the lower part of the shuttle shaft and the rod for the drive of the thread deflector, the housing shaft will have an especially small cross section.

To avoid a collision between the main blade and the thread loop during the pivoting movement of the main blade of the shuttle from its position holding the thread loop into the position necessary for performing its lowering movement, which pivoting movement takes place above the material being sewn, the thread deflector has an essentially V-shaped, obliquely upwardly directed receiving groove for the upper leg of the thread loop, whose oblique position extends essentially in parallel to the thread loop to facilitate the grasping of the leg of the thread loop at the time of the reception of the leg of the thread loop. Due to the horizontal movement component that can be imparted at the same time to the thread deflector, the thread loop is additionally removed from the path of movement of the main blade.

To secure the thread loop grasped by the main blade of the shuttle during its pivoting movement, the shuttle has a counterblade, whose tip is directed essentially opposite the tip of the main blade.

Further details and advantages will appear from the following description of a preferred embodiment of the present invention, which is shown in the drawings attached. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 1 is a general schematic view of an endoscopic suturing machine;

FIG. 1a is an enlarged view of a detail "A" of FIG. 1;

FIG. 5a is a somewhat enlarged view of a detail of the horizontal drive 80 for the shuttle 12;

FIG. 5b is an enlarged view of a detail of the deflector drive for the thread deflector 13;

FIG. 6a is a top view of the shuttle 12;

FIG. 6b is a side view of the shuttle 12;

FIG. 6c is an enlarged perspective view of the shuttle 12;

FIG. 7 is a view of the lifting and lowering means for the holding-down device 14;

FIG. 7a is an enlarged view of a detail "B" of FIG. 7;

FIG. 7b is an enlarged view of a detail "C" in FIG. 7;

DESCRIPTION OF THE PREFERRED EMBODIMENT

Figure 2:
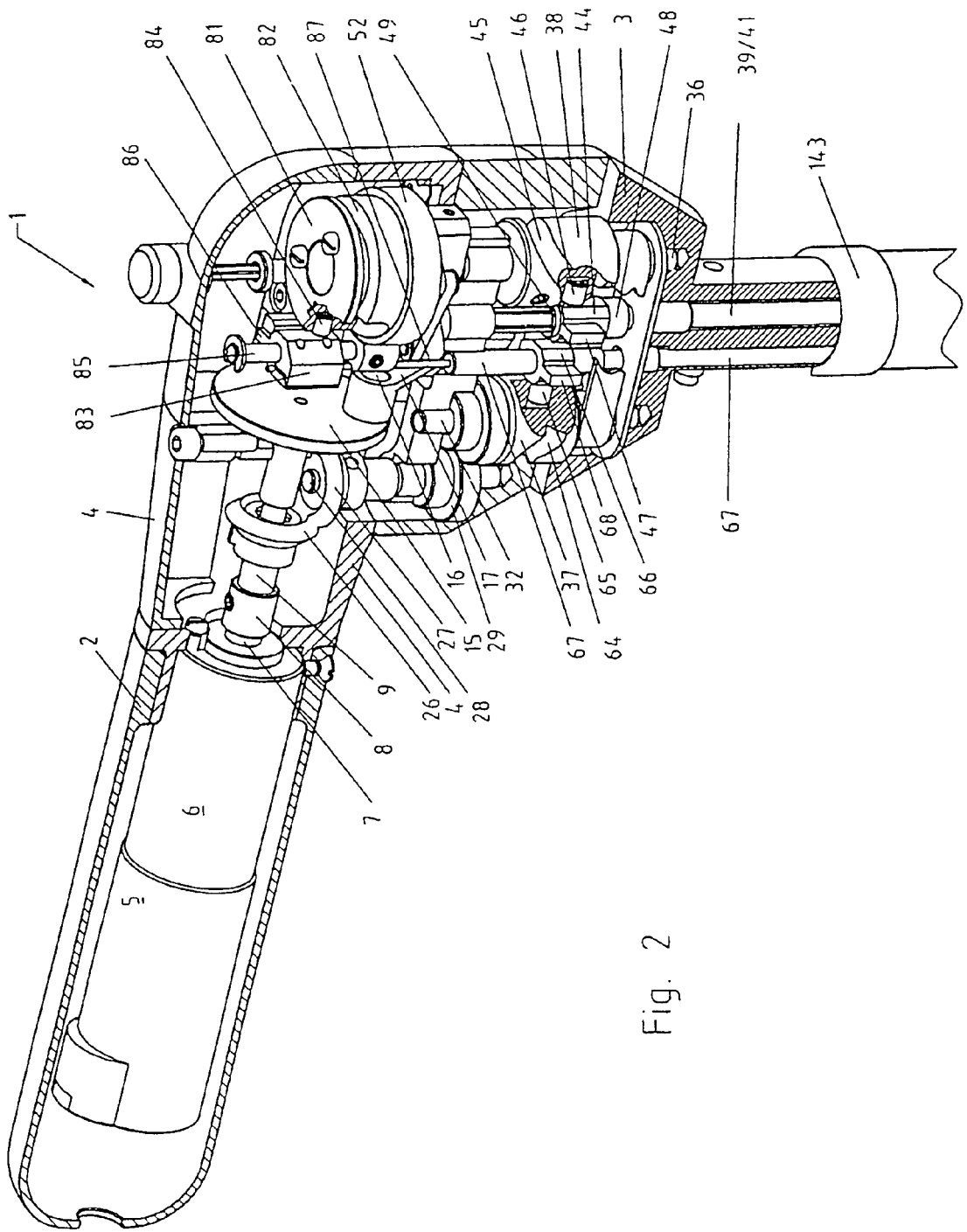
FIG. 2 is a partially cut-away view of the grip part and the middle part of the housing.

Referring to the drawings in particular, the endoscopic suturing machine 1 schematically shown in FIG. 1 has an essentially L-shaped housing, which is formed by a grip part 2 designed as a hollow body, a housing shaft 3 directed essentially at right angles to the grip part, and a housing middle part 4 connecting the housing shaft to the grip part 2.

Figure 3:
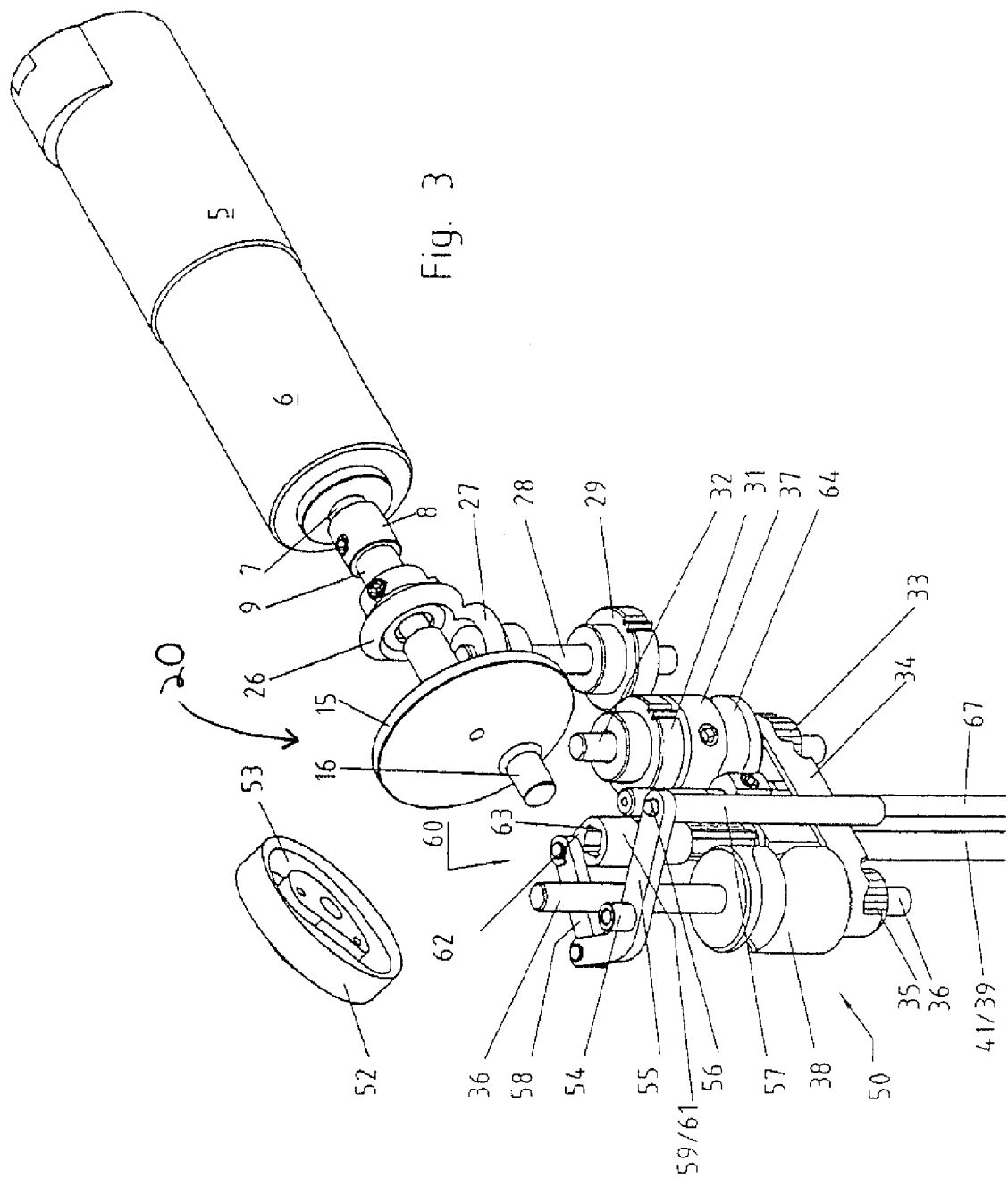
FIG. 3 is a diagram of the lifting and pivoting drive as well as part of the horizontal drive for the shuttle shaft.
Figure 4:
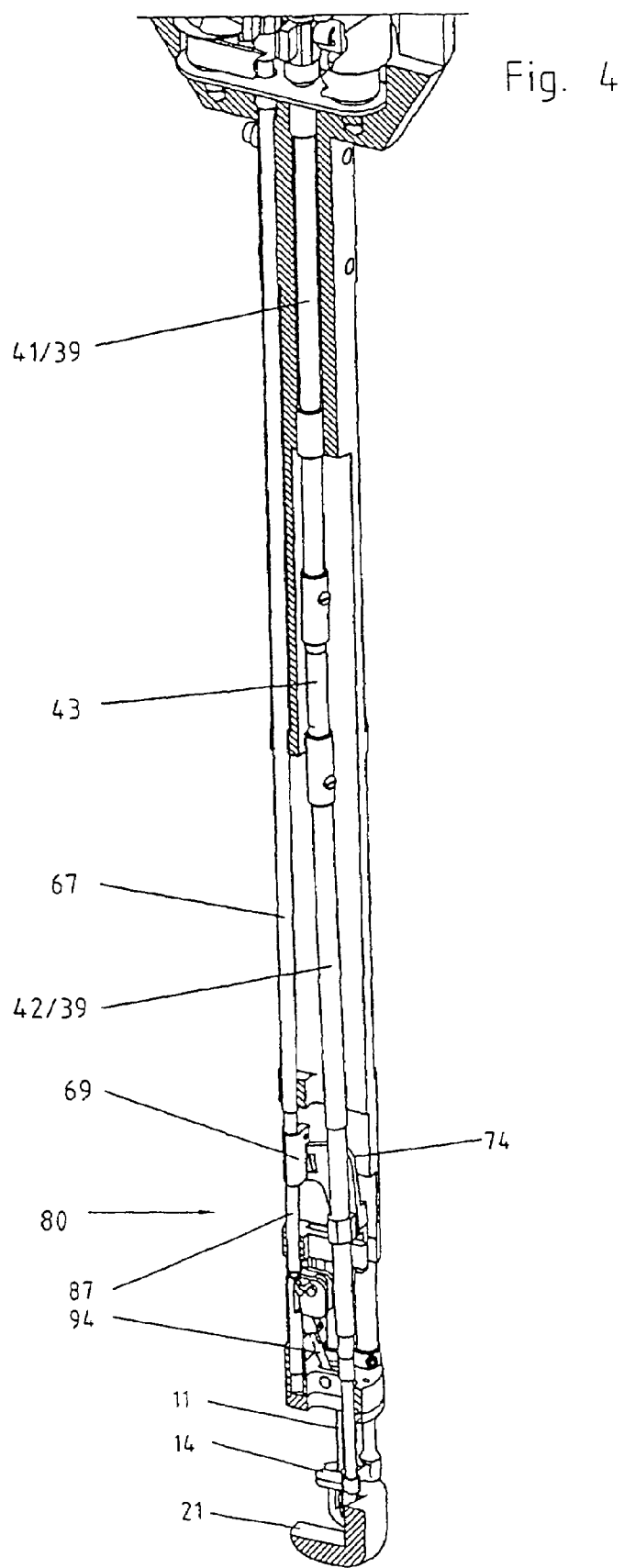
FIG. 4 is a view of the housing shaft 3 with the protective tube removed.

An electric motor, which is preferably designed as a d.c. motor 5, is arranged within the grip part 2 (FIGS. 2 and 3). The driven shaft of the d.c. motor 5, not shown, is rigidly connected to an input shaft, likewise not shown, of a reducing gear 6, which is preferably designed as a planet gear and is arranged within the grip part 2 and whose driven shaft 7 is connected to a main shaft 9 by means of a prior-art cut-off coupling 8 in the known manner. The main shaft 9, from which the movements for the needle 11 and a shuttle 12 as well as for a thread deflector 13 cooperating with the shuttle and for a holding-down device 14 are derived, is mounted floatingly in the housing middle part 4 and carries at its free end a crank disk 15, on the pin 16 of which a deflector 17 acts, and the deflector 17 is in turn articulated to a needle bar 18 carrying the needle. The above-described parts form a needle drive 20.

Holes directed in parallel to the longitudinal axis of the crank disk 15 or other marks may be provided on the crank disk 15 for the optical detection of the speed and/or angle of rotation of the main shaft 9. The connection between the deflector 17 and the needle bar 18 may be designed as a detachable connection in a known manner in order to make it possible as a result to set the position of the lower or upper reversal points of the movement of the needle 11.

The needle bar 18 is guided in guides 19 provided on the housing shaft 3 in the direction of its longitudinal axis and performs vertically directed lifting movements, with the tip of the thread-carrying needle 11 passing through a slot-like stitch hole 22 provided on a needle plate 21. The needle plate 21 is formed in the area of the lower end of the housing shaft 3 at the housing shaft, and its lateral edge 23 extends at a certain laterally spaced location from the stitch hole 22. The needle bar 18 is arranged somewhat offset to the side of the main shaft 9 for design reasons in the exemplary embodiment being shown.

Since a chain stitch suture of the stitch type 501 or of a similar stitch type is to be prepared with the suturing machine according to the present invention, and a single-shuttle system is used for this instead of the generally common two-shuttle system for reasons of saving space, its shuttle 12 must perform, as will be explained later, a three-dimensional movement, which is composed of a vertical movement, a pivoting movement and an essentially horizontally directed oscillating movement.

A bevel gear 26, which is arranged on the main shaft 9 and engages a mating gear 27, which is mounted on an intermediate shaft 28 mounted in the housing middle part 4, is provided for driving the shuttle 12. The intermediate shaft carries at its lower end a spur gear 29, which meshes with a mating gear 31. The latter is arranged on a shaft 32, which is likewise mounted in the housing middle part 4 and whose lower end carries a toothed belt pulley 33, which engages a mating gear 35 via a toothed belt 34. This mating gear 35 is arranged on a shaft 36, which is directed in parallel to the shaft 32 and is likewise mounted in the housing middle part 4. The two shafts 32 and 36 thus run in the same direction.

A cylinder cam 37 is arranged on the shaft 32 above the toothed belt pulley 33, and a cylinder cam 38 is arranged on the shaft 36. While the cylinder cam 37 is used to generate an oscillating movement of the shuttle 12 in a manner to be described later, the cylinder cam 38 is used to generate the lifting movement of the shuttle 12 and consequently for a lifting movement of a shuttle shaft 39, which carries the shuttle and is arranged essentially in parallel to the shafts 32, 36. This shuttle shaft has a two-part design and comprises an upper part 41 and a lower part 42 carrying the shuttle 12. A hinge piece 43, which, though permitting a relative movement between the upper part 41 and the lower part 42 within a vertical plane, connects the upper part 41 to the lower part 42, which rotate in unison, is used to connect the upper part 41 mounted rotatably and longitudinally displaceably in the housing middle part 4 to the lower part 42.

A carrier 44 for a tracing roller 46 protruding into a cam groove 45 of the cylinder cam 38 is arranged on the upper part 41 of the shuttle shaft 39, and the vertical movements of the tracing roller are transmitted via the carrier 44 to the upper part 41. To transmit the axial movement of the carrier 44 to the shuttle shaft 39, the carrier is arranged between an adjusting ring 48 clamped onto the upper part 41 and a butting ring 49 fastened at a spaced location thereto on the upper part 41.

The shuttle shaft 39 is freely rotatable at the carrier 44. The carrier 44 has a prismatic projection 47, which slides in a groove (not shown in greater detail) of the housing middle part 4 and secures the carrier 44 against torsion.

Together with the parts arranged between it and the upper part 41 of the shuttle shaft 39, the cylinder cam 38 forms a lifting drive 50 for these parts.

To achieve a pivoting movement of the shuttle 12, an additional cam plate 52, which has on its lower face a groove 53 that is engaged by a tracing roller 54, is arranged on the shaft 36 above the cylinder cam 38.

The tracing roller 54 is arranged between the ends of a lever 55, one end of which is pivotable around a pin 56, which is directed in parallel to the shaft 36 and is in turn mounted in a bush 57, which is fastened in the housing middle part 4. A connecting rod 58, which is connected to a rocker 59 in an articulated manner, is articulated to the still free end of the lever 55. The rocker 59 is formed by a bush 61, which is arranged at the upper end of the upper part 41 of the shuttle shaft 39 and has a lever arm-like projection 62 for the action of the connecting rod 58. The rocker 59 is connected to the upper part 41 of the shuttle shaft 39, rotating in unison with it, the shuttle shaft having in the area of its upper end for this purpose a spline profile 63, which engages a mating profile (not designated specifically) provided in the bush 61. The spline profile 63 cooperating with the mating profile guarantees, on the one hand, the connection between the rocker 59 and the upper part 41 of the shuttle shaft 39, which connection rotates in unison, and, on the other hand, the spline profile 63 slides in the rocker 59 fixed in the axial direction during the lifting movements of the shuttle shaft 39, which are initiated by the lifting drive 50. The movements of the lever 55, which are derived from the cam plate 52 via the above-mentioned gear mechanism, thus bring about a pivoting movement of the shuttle shaft 39 around its own axis, without compromising its axial mobility. The gear mechanism from the cam plate 52 to the shuttle shaft 39 or to the shuttle 12 forms a pivoting drive 60 for the shuttle 12 or for the shuttle shaft 39.

To achieve the oscillating movement of the lower part 42 of the shuttle shaft 39, the above-mentioned cylinder cam 37 has a cam groove 64 for a tracing roller 65, whose vertical movements are transmitted via a carrier 66 accommodating the tracing roller 65 to a push rod 67, which is designed as a tube for a purpose to be explained later. The carrier 66 has a prismatic projection 68, which slides in a groove (not shown in detail) of the housing middle part 4 and secures the carrier 66 against rotation.

Figure 5:
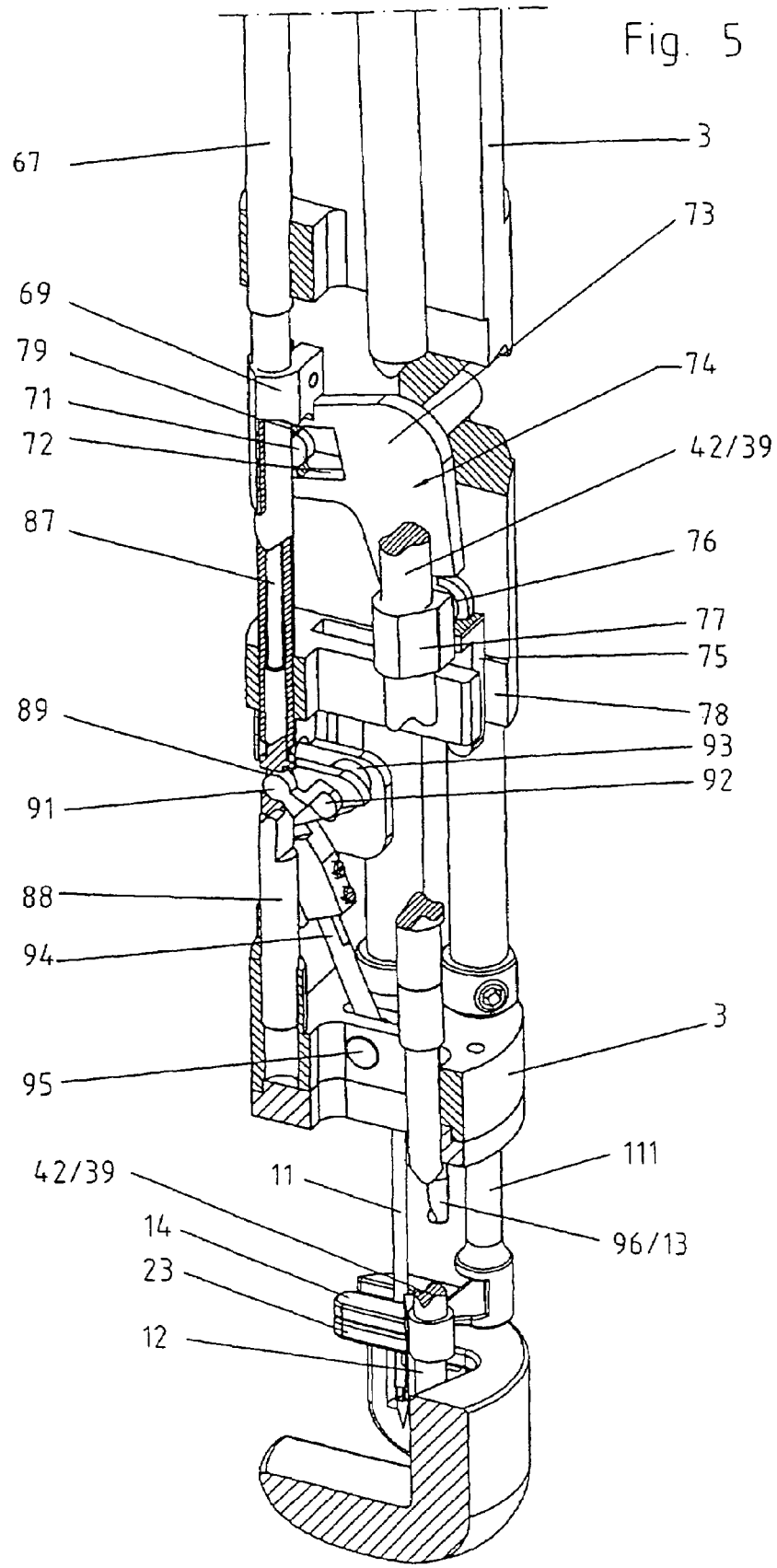
FIG. 5 is an enlarged view of the lower area of the housing shaft.

The push rod 67 is guided in the housing shaft 3 and has, in the area of its lower end (FIG. 5), a pin 71, which is carried by a clamping piece 69, is directed at right angles to the push rod 67 and carries a sliding block 79. This sliding block slides within a guide groove 72, which is formed on an arm 73 of an angle lever 74 mounted in the housing shaft 3.

The other arm 75 of the angle lever 74 carries a hinge piece 76, which is connected to a sleeve 77 arranged longitudinally displaceably on the lower part 42 of the shuttle shaft 39.

As a result, an oscillating movement of the lower part 42 of the shuttle shaft 39 around the hinge piece 43 arranged between the lower part and the upper part 41 of the shuttle shaft 39 is derived from the lifting movement of the push rod 67. Due to the relatively great pivoting radius for the lower part 42, the lifting component of this oscillating movement is functionally negligible, so that the oscillating movement of the lower part 42 derived from the push rod 67 can be considered to be a horizontal movement. To ensure the reliable guiding of the lower part 42 of the shuttle shaft 39, the arm 75 of the angle lever 74 may be extended beyond the hinge piece 76, and it may slide within a guide groove 78 provided in the housing shaft 3. As a result, the lower part 42 of the shuttle shaft 39 is secured against forces directed at right angles to its horizontal movement.

The gear connection from the cylinder cam 37 to the lower part 42 of the shuttle shaft 39 is called the horizontal drive 80 of the shuttle shaft 39 or the shuttle 12.

An additional cam plate 81, which has a cam groove 82 for a tracing roller 84 accommodated by a carrier 83, is arranged above the cylinder cam 38 (FIG. 2) on the shaft 36 accommodating the cylinder cam 38. The carrier 83 is mounted longitudinally displaceably on an essentially vertically directed guide pin 85, which is fastened in the housing middle part 4, and has a prismatic projection 86, which protrudes into a guide groove (not shown in greater detail) provided in the housing middle part 4 and secures the carrier 83 against torsion.

A rod 87, which is led through the push rod 67 designed as a tube to the lower end of the push rod, is fastened to the carrier 83. In the area of its lower end, the rod 87 is connected to a pin 88 (FIG. 5), which is guided axially in a bearing (not shown) provided in the housing shaft 3. An essentially rectangular opening 89 is provided in the pin 88, and the free end of a disk-shaped lever 91, which is arranged on a shaft 92, which is mounted in the housing shaft 3 and is directed essentially horizontally, protrudes into the opening. As a result, the lifting movement of the pin 87, which is initiated by the cam plate 81, is converted into a pivoting movement of the lever 91 and consequently of the shaft 92.

A crank 93, to which one end of a sliding bar 94 is articulated, is arranged on the shaft 92 (FIG. 5b), the sliding bar 94 being arranged displaceably in a rotary sliding joint 95 mounted in the housing shaft 3. A shaft 96 of the thread deflector 13 proper, which is provided with a receiving groove 97, which has an essentially V-shaped design and has an obliquely directed support surface 98 for the thread loop, is formed at the still free end of the sliding rod 94 for the upper leg of the thread loop. The shaft 96 is directed essentially in parallel to the shuttle shaft 39, and the oblique position of its receiving groove 97 is selected to be such that it extends essentially in parallel to the thread loop at the time at which the thread loop is taken up. Due to the above-described gear arrangement, the thread deflector 13 performs a movement composed of a vertical component and a horizontal component, the horizontal component being directed essentially in parallel to the direction of the suture to be formed.

The cam plate 81 forms a deflector drive 100 for the thread deflector 13 together with the parts arranged between it and the shaft 96.

The shuttle 12 (FIGS. 6a, 6b and 6c) arranged at the lower end of the shuttle shaft 39 is firmly connected to the shuttle shaft and thus participates in all movement components (vertical movement, pivoting movement and horizontally directed oscillating movement) of the shuttle shaft 39.

The shuttle has an area 101, which is directed essentially in parallel to the axis of its mounting hole and which is joined by a shaft 102. The shaft 102 passes over into a web 103, at the free end of which a main blade 104 receiving the thread loop formed under the material being sewn in the usual manner is provided with a tip 105. A counterblade 106, whose tip 107 is directed essentially opposite the tip 105 of the main blade 104, is formed on the shaft 102 opposite the main blade 104. The counterblade 106 is used, in a manner yet to be described, to prevent the thread loop grasped by the main blade 104 from slipping off and has a receiving groove 108 extending over its entire width for the lower leg of the thread loop in the area of its transition to the shaft 102.

The holding-down device 14 (FIGS. 7, 7a and 7b) used to fix the material being sewn on the needle plate 21 is arranged at the lower end of a push rod 111, which is arranged displaceably in the housing shaft 3 and is directed essentially in parallel to the needle bar 18. To make it possible to periodically raise the holding-down device 14 by a certain amount during at least part of the phase during which the needle 11 is located outside the material being sewn in order to facilitate the feed motion of the material being sewn, a carrier 112 is arranged on the needle bar 18, and the carrier extends under a stop 113 fastened in the upper area of the push rod 111 and carries this stop at least during part of the lifting movement of the needle bar 18. The position of the carrier 112 on the needle bar 18 may be selected to be such that the holding-down device 14 is raised and lowered symmetrically to the upper reversal point of the needle.

The stop 113 has a fork-shaped design at its end facing away from the push rod 111 and surrounds with this end the needle bar 18, as a result of which the push rod 111 is also secured at the same time against rotary movements. The area of the stop 113 surrounding the push rod 111 is used at the same time to support the lower end of a compression spring 114, whose upper end is supported against a bush 115, which is in turn in contact with the underside of a threaded bush 116. This cooperates with an internal thread provided in the housing shaft 3. For the axial displacement of the threaded bush 116 and consequently for changing the force of the compression spring 114, the threaded bush 116 is provided with a hexagon socket, not shown in greater detail, and a rod 117 passes through it, which has a cross section corresponding to the hexagon socket. Even though the rod 117 is arranged longitudinally displaceably within the threaded bush 116, it is connected to it in such a way that it rotates in unison with it. A spur gear 118, which rotates in an essentially horizontal plane and meshes with a mating gear 119, is provided in the housing shaft 3 above the threaded bush 116. The rod 117 likewise passes through the spur gear 118, but the cross section of this rod may be smaller than the axial hole 121 provided for it in the spur gear 118, because the rod 117 is led freely only through the spur gear 118. The mating gear 119 is connected to an axle 122, which is mounted in the housing middle part 4 and is directed essentially in parallel to the push rod 111. The axle 122 fixed axially in the housing middle part 4 carries at its upper end an adjusting handle 123, which is arranged outside the housing middle part 4. By rotating the adjusting handle 123, the threaded bush 116 and consequently the bush 115 are axially displaced within the housing shaft 3, and the force of the compression spring 114 is changed by the change in the length of the spring, which is associated therewith.

An essentially horizontally directed axle 124, to which both an additional handle 125 projecting from the housing middle part 4 and a pivoted lever 126 are firmly connected, is mounted in the housing middle part 4 for raising and lowering the holding-down device 14 manually. The pivoted lever 126, which is bent at its free end has a fork-shaped design, extends under a collar 127 of a bush 128, which surrounds the axle 122 but is not connected to it and carries a strap 129 firmly connected to it at its lower end. Even though the axle 122 is led through the strap 129, it is freely rotatable independently from the strap 129. At its still free end, the strap 129 is connected to the end of the rod 117 protruding from the spur gear 118. This connection is such that the rod 117 is freely rotatable in relation to the strap 129, but the two are firmly connected to one another in the axial direction.

The end of the rod 117 protruding from the bush 115 is led through the compression spring 114 up to the stop 113, and it brings about the centering of the rod. A threaded pin 132, which is provided with a collar 131 and whose upper end can in turn be screwed into a threaded sleeve 133, is screwed into the upper end of the push rod 111. The threaded sleeve 133 is provided with an axially directed hole 134, through which the lower end of the rod 117 is led, and is axially fixed in the threaded sleeve 133 by means of a collar 135 provided on the rod 117.

Since the fork-shaped end of the stop 113 extends under the collar 131 of the threaded pin 132, the holding-down device 14 can be raised and lowered manually by pivoting the handle 125.

To feed a thread reserve site located outside the housing to the needle 11, a hole 141 (FIG. 7) is provided at the housing shaft 3, and the hole 141 opens into a thread guide tube 142 arranged within the housing shaft 3. The thread leaves the thread guide tube 142 at the lower end of this thread guide tube 142 and is led from there to the needle 11.

The housing shaft 3 as well as all the functional parts arranged on and in same are surrounded by a protective tube 143, which can be pushed over the housing shaft 3 and can be fixed in the upper area of the housing shaft 3.

Since both the stitch-forming tools 11, 12 and the needle plate 21 and the holding-down device 14 as well as the thread deflector 13 are not supposed to protrude in relation to the protective tube 143 when the housing shaft 3 is introduced into the body, but they shall rather be retracted into the housing shaft, the protective tube 143 can be locked at the housing shaft 3 in a first position, in which it protrudes in relation to the above-mentioned functional parts. To form the suture, the protective tube 143 can be locked in a second position, in which the above-mentioned functional parts will in turn protrude in relation to the protective tube 143. Both locked positions of the protective tube 143 may be arranged in the upper area of the housing shaft 3 and be formed by spring-loaded balls in the usual manner.

Figure 8:
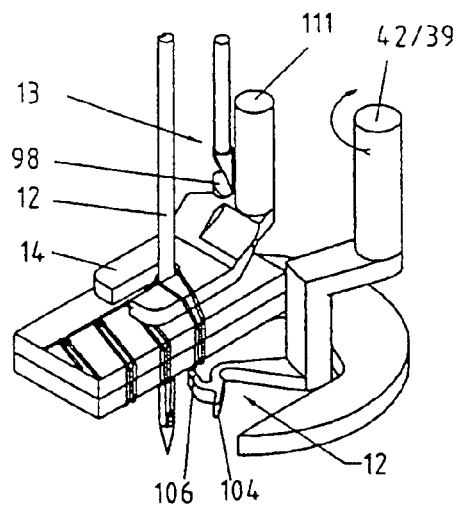
FIG. 8 is a diagram of the needle, the shuttle, the holding-down device and the thread deflector with the course of the thread with the needle in the area of its bottom dead center before the loop lift.

The stitch formation will be explained below on the basis of the bottom dead center of the needle 11, which is shown in FIG. 8.

The needle 11, driven by the needle drive 20 in the known manner, has pierced the thread loop led upward by the shuttle 12 and holds same above the holding-down device 14. The shuttle shaft 39 and the shuttle 12 connected to same are still performing now their downwardly directed movement, and the main blade 104 of the shuttle 12 and consequently the tip 105 of the main blade 104 are being pivoted at the same time by the pivoting drive 60—in reference to FIG. 8—toward the needle 11 in the direction of the arrow shown in FIG. 8. This pivoting movement will hereinafter be called a "clockwise" pivoting movement of the shuttle 12 and of the shuttle shaft. The hinge piece 43 is now deflected such that the lower part 42 of the shuttle shaft 39 is located in the area of the end of its horizontally directed deflecting movement, which end faces away from the needle 11. The thread deflector 13 is now in its upper position, which corresponds to its inoperative position.

While the loop lift of the needle 11 is being carried out, the tip 105 of the main blade 104 is moved, in continuation of its clockwise pivoting movement, into the thread loop formed under the needle plate 21 by the pivoting drive 60, so that the thread loop is taken up by the main blade 104 and hangs on same. The thread deflector 13 continues to be in its inoperative position. The horizontal drive 80 has begun to push the lower part 42 of the shuttle shaft 39 in the direction of the needle 11, as a result of which the thread loop is moved on the main blade 104 in the direction of the shaft 102 of the shuttle 12.

Figure 9:
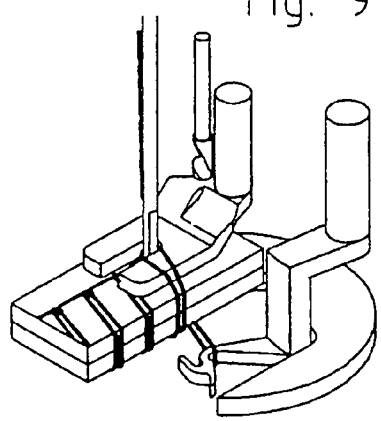
FIG. 9 is a view corresponding to FIG. 8 with the shuttle located to the side of the material being sewn before its upward movement.

During the further course of the stitch formation, the shuttle 12 is pivoted with the thread loop taken up by the main blade 104 by the pivoting drive 60 in the counterclockwise direction, and it reaches a position located to the side of the material being sewn (FIG. 9). The lifting drive 50 subsequently moves the shuttle 12 from its position that is located below the material being sewn in terms of height into a level located above the material being sewn, in which the main blade 104 is located in a kind of intermediate position in terms of height.

Figure 10:
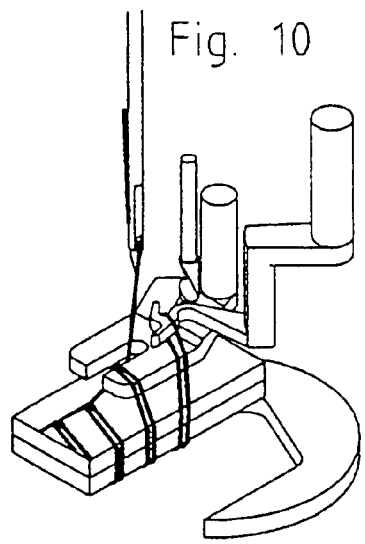
FIG. 10 is a view corresponding to FIG. 8 with the needle in the area of its top dead center.

The lifting movement of the shuttle 12 continues from this point while the pivoting drive 60 begins to function at the same time, so that the main blade 104 is raised farther and is led at the same time behind the axis of the needle 11, which has meanwhile been moved upward. The main blade 104 now crosses the plane of the path of movement of the needle 11, which is located in the area of its top dead center FIG. 10). With the holding-down device 14 raised by the needle bar 18, a manual feed motion of the material being sewn takes place during this clockwise pivoting movement.

Figure 11:
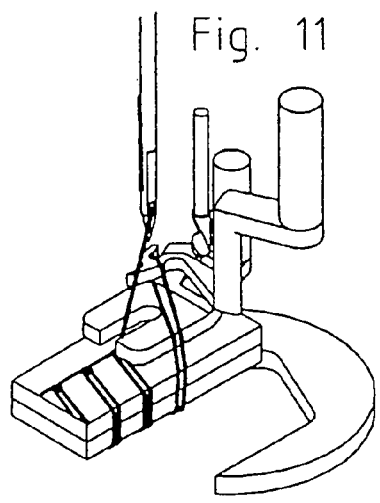
FIG. 11 is a view corresponding to FIG. 8 with the needle located about 20° to 40° after its top dead center.

The thread loop, which is still being carried by the main blade 104, lies at the end of the material being sewn and extends from there to the tip 105 of the main blade 104. The thread loop now tends to slip off from the main blade 104. This is prevented by the counterblade 106, and one of the legs of the thread loop slides into the receiving groove 108 of the counterblade 106 and is fixed in same. The thread deflector 13 still continues to be in its inoperative position. The horizontal drive 80 deflects the lower part 42 of the shuttle shaft 39 in the direction of the needle 11, and the thread loop hanging on the main blade 104 is moved toward the axis of the needle 11. The needle 11, which is performing its downwardly directed movement, is inserted into the thread triangle spread due to the oblique position of the receiving groove 108 of the shuttle 12 (FIG. 11).

After the thread loop has been cut off by the needle 11, the horizontal drive 80 moves the lower part 42 of the shuttle shaft 39 opposite the direction of its previous movement away from the needle 11 in the direction of its rear reversal point. As a result, the path of movement becomes free for a counterclockwise pivoting movement of the main blade 104 to avoid a collision between it and the needle 11, so that the main blade 104 can be moved by the pivoting drive 60 from its position that is located behind the axis of the needle 11 relative to the edge of the material being sewn into a position located on the side of the edge of the material being sewn.

Before the beginning of this pivoting movement of the main blade 104, the obliquely downwardly directed movement of the thread deflector 13 begins, which is brought about by the deflector drive 100, as a result of which the upper leg of the thread loop is grasped by the thread deflector 13 and is fixed by the V-shaped receiving groove 97 of the thread deflector. The grasped leg of the thread loop now lies on the oblique surface 98 of the thread deflector 13. This thread deflector subsequently performs its working movement removing the thread loop from the area of the main blade 104 and displaces the upper leg of the thread loop in the direction of suturing. As a result, the main blade 104 can be pivoted by the pivoting drive 60 in the counterclockwise direction without colliding in the process with the thread loop being carried by the thread deflector 13.

Figure 12:
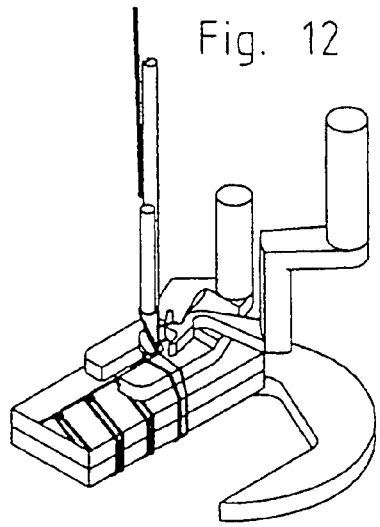
FIG. 12 is a view corresponding to FIG. 8 with the needle located about 120° after its top dead center.

As soon as the main blade 104 has moved beyond the thread loop still being carried by the thread deflector 13 (FIG. 12), the thread deflector 13 is returned by the deflector drive 100 into its inoperative position. Since this is formed by a vertical movement component and a horizontal movement component and the horizontal component is directed in the direction of the tip of the receiving groove 97, the thread loop slips off from the support surface 98 of the receiving groove 97 at the beginning of the reverse movement of the thread deflector 13; the thread deflector 13 now returns into its inoperative position. At the same time, the horizontal drive 80 displaces the lower part 42 of the shuttle shaft 39 to the reversal area of its deflecting movement, which area faces away from the needle 11. As soon as the shuttle 12 has completed its counterclockwise pivoting movement, the lifting drive starts to operate and returns the shuttle 12 into its pivoting plane located under the material being sewn. The stitch formation operation can now be repeated.

While specific embodiments of the invention have been shown and described in detail to illustrate the application of the principles of the invention, it will be understood that the invention may be embodied otherwise without departing from such principles.

The invention claimed is:

1. An endoscopic suturing machine, comprising:
    drives;
    stitch formation tools including at least one thread-carrying needle and a shuttle cooperating with same;
    a housing with a housing upper part for accommodating said drives and a housing shaft adjoining said housing upper part; and
    transmission means including a pivoting drive and a lifting drive associated with a shuttle shaft with cam plates arranged on one and the same shaft for transmitting movements generated by said drives to said stitch-forming tools, said housing shaft accommodating said transmission means, said transmission means moving said shuttle from a position under a material being sewn via a first pivoting movement, said transmission means lifting said shuttle with a thread loop at a spaced location from the material being sewn and pivoting said shuttle with said thread loop into a position above the material being sewn via a second pivoting movement, whereby a thread triangle formed by the thread loop surrounds a projection of a path of said needle.

2. An endoscopic suturing machine in accordance with claim 1, wherein the first pivoting movement of said shuttle is used to grasp the thread loop and takes place around an axle, wherein distance between said axle and said needle during said first pivoting movement of said shuttle is greater than distance between said axle and needle during said second pivoting movement of said shuttle.

3. An endoscopic suturing machine in accordance with claim 1, wherein a driven part of said lifting drive is rigidly connected in an axial direction to said shuttle shaft, and said shuttle shaft is freely rotatable in said driven part.

4. An endoscopic suturing machine in accordance with claim 3, wherein a driven part of said pivoting drive is connected to said shuttle shaft to rotate in unison with said shuttle shaft and said shuttle shaft is longitudinally displaceable in an axial direction in the driven part.

5. An endoscopic suturing machine in accordance with claim 1, wherein transmission means includes a shuttle shaft formed by an upper part and a lower part connected to one another by a hinge piece such that said lower part is movable in the horizontal direction in relation to said upper part.

6. An endoscopic suturing machine in accordance with claim 5, wherein to achieve a relative movement between said upper part and said lower part a horizontal drive is provided, which brings about a lifting movement of a push rod, which movement is derived from a cam plate and can be transmitted as a horizontal movement to said lower part via a drive connection, said drive connection including pivoting and lifting drives.

7. An endoscopic suturing machine in accordance with claim 6, wherein said cam plate of said horizontal drive is arranged on a shaft directed in parallel to a lifting drive shaft and carries an additional cam plate for driving a thread deflector above the cam plates for the pivoting and lifting drives.

8. An endoscopic suturing machine in accordance with claim 7, wherein said cam plate actuates a rod which is arranged within a push rod longitudinally displaceably, and an end of said rod protruding from said push rod imparts a movement having a vertical movement component and a horizontal movement component on a thread deflector via a drive connection.

9. An endoscopic suturing machine in accordance with claim 1, further comprising a thread deflector with an essentially V-shaped, obliquely upwardly directed receiving groove for one leg of the thread loop, wherein an oblique position of said receiving groove extends in parallel to the thread loop at the time at which the thread loop is taken up.

10. An endoscopic suturing machine in accordance with claim 1, wherein said shuttle has a counterblade with a tip directed opposite a tip of a shuttle main blade.

11. An endoscopic suturing machine, comprising:
    a plurality of drives;
    stitch formation tools including at least one thread-carrying needle and a shuttle cooperating with same;
    a housing with a housing upper part for accommodating said drives and a housing shaft adjoining said housing upper part; and
    transmission means for transmitting movements generated by said drives to said stitch-forming tools, said transmission means including a pivoting drive and a lifting drive associated with a shuttle shaft with cam plates arranged on one and the same shaft and directed in parallel to said shuttle shaft, said housing shaft accommodating said transmission means, said transmission means moving said shuttle from a position under a material being sewn and pivoting said shuttle with a thread loop into a position above the material being sewn, in which a thread triangle formed by the thread loop surrounds a projection of a path of said needle.

12. An endoscopic suturing machine, comprising:
    a plurality of drives;
    stitch formation tools including at least one thread-carrying needle and a shuttle cooperating with same;
    a housing with a housing upper part for accommodating said drives and a housing shaft adjoining said housing upper part; and
    transmission means for transmitting movements generated by said drives to said stitch-forming tools, said transmission means including a pivoting drive and a lifting drive associated with a shuttle shaft with cam plates arranged on one and the same shaft, said housing shaft accommodating said transmission means, said transmission means moving said shuttle from a position under a material being sewn to a first location spaced from the material being sewn, said transmission means lifting said shuttle with a thread loop from said first location to a second location spaced from the material being sewn and pivoting said shuttle with said thread loop into a position above the material being sewn, whereby a thread triangle formed by the thread loop surrounds a projection of a path of said needle.

13. An endoscopic suturing machine, comprising:
drives;
stitch formation tools including at least one thread-carrying needle and a shuttle cooperating with same;
a housing with a housing upper part for accommodating said drives and a housing shaft adjoining said housing upper part; and
a transmission means including a pivoting drive and a lifting drive associated with a shuttle shaft with cam plates arranged on one and the same shaft for transmitting movements generated by said drives to said stitch-forming tools, said shuttle being connected to said shuttle shaft, said shuttle shaft being arranged in said housing such that said shuttle shaft is longitudinally displaceable and rotatable, said pivoting drive and said lifting drive being parallel to said shuttle shaft, said housing shaft accommodating said transmission means, said transmission means moving said shuttle from a position under a material being sewn via a first pivoting movement, said transmission means lifting said shuttle with a thread loop at a spaced location from the material being sewn and pivoting said shuttle with said thread loop into a position above the material being sewn via a second pivoting movement, whereby a thread triangle formed by the thread loop surrounds a projection of a path of said needle.

14. An endoscopic suturing machine, comprising:
drives;
stitch formation tools including at least one thread-carrying needle and a shuttle cooperating with same;
a housing with a housing upper part for accommodating said drives and a housing shaft adjoining said housing upper part; and
a transmission means including a pivoting drive and a lifting drive associated with a shuttle shaft with cam plates arranged on one and the same shaft for transmitting movements generated by said drives to said stitch-forming tools, said housing shaft accommodating said transmission means, said transmission means moving said shuttle from a position under a material being sewn via a first pivoting movement, said transmission means lifting said shuttle with a thread loop at a spaced location from the material being sewn and pivoting said shuttle with said thread loop into a position above the material being sewn via a second pivoting movement, whereby a thread triangle formed by the thread loop surrounds a projection of a path of said needle, wherein a driven part of said pivoting drive is connected to said shuttle shaft to rotate in unison with said shuttle shaft and said shuttle shaft is longitudinally displaceable in an axial direction in the driven part.

15. An endoscopic suturing machine, comprising:
drives;
stitch formation tools including at least one thread-carrying needle and a shuttle cooperating with same;
a housing with a housing upper part for accommodating said drives and a housing shaft adjoining said housing upper part;
a drive connection; and
transmission means including a pivoting drive and a lifting drive associated with a shuttle shaft with cam plates arranged on one and the same shaft for transmitting movements generated by said drives to said stitch-forming tools, said shuttle shaft having an upper shaft portion and a lower shaft portion, said housing shaft accommodating said transmission means, said transmission means moving said shuttle from a position under a material being sewn via a first pivoting movement, said transmission means lifting said shuttle with a thread loop at a spaced location from the material being sewn and pivoting said shuttle with said thread loop into a position above the material being sewn via a second pivoting movement, whereby a thread triangle formed by the thread loop surrounds a projection of a path of said needle, said transmission means including a horizontal drive for providing a push rod with a lifting movement such that said upper portion and said lower portion of said shuttle shaft move relative to one another, said drive connection transmitting said lifting movement as a horizontal movement to said lower part of said shuttle shaft.

16. An endoscopic suturing machine, comprising:
drives;
stitch formation tools including at least one thread-carrying needle and a shuttle cooperating with same;
a housing with a housing upper part for accommodating said drives and a housing shaft adjoining said housing upper part;
a drive connection;
a thread deflector; and
transmission means including a pivoting drive and a lifting drive associated with a shuttle shaft with cam plates arranged on one and the same shaft for transmitting movements generated by said drives to said stitch-forming tools, said housing shaft accommodating said transmission means, said transmission means moving said shuttle from a position under a material being sewn via a first pivoting movement, said transmission means lifting said shuttle with a thread loop at a spaced location from the material being sewn and pivoting said shuttle with said thread loop into a position above the material being sewn via a second pivoting movement, whereby a thread triangle formed by the thread loop surrounds a projection of a path of said needle, one of said cam plates being a thread deflector cam plate for driving said thread deflector, said thread deflector cam plate actuating a first rod arranged longitudinally displaceably within a push rod such that an end of said first rod imparts a vertical movement component and a horizontal movement component on said thread deflector via said drive connection.

* * * * *